United States Patent [19]

Shaffer et al.

[11] Patent Number: 5,555,768

[45] Date of Patent: Sep. 17, 1996

[54] METHOD AND APPARATUS FOR TESTING A MEDICINAL TABLET

[75] Inventors: Donald R. Shaffer, Acme; Richard A. Sanderson, McKeesport; John Savko, Irwin, all of Pa.

[73] Assignee: Elizabeth-Hata International, Inc., North Huntingdon, Pa.

[21] Appl. No.: 409,760

[22] Filed: Mar. 24, 1995

[51] Int. Cl.⁶ ........................................ G01B 5/00
[52] U.S. Cl. ............................. 73/865.8; 73/821
[58] Field of Search .................... 73/865.8, 821, 73/81, 82; 198/468.1, 468.8, 468.9, 737, 741; 248/92, 95; 177/145, 161

[56] References Cited

U.S. PATENT DOCUMENTS

| | | | |
|---|---|---|---|
| 4,393,717 | 7/1983 | Mason et al. | 73/821 |
| 4,466,532 | 8/1984 | Minneman et al. | 198/468.01 |
| 4,641,534 | 2/1987 | Schneider et al. | 73/856 |
| 4,651,203 | 3/1987 | Peterson | 348/95 |
| 4,660,713 | 4/1987 | Kaminski | 198/443 |
| 4,807,465 | 2/1989 | Botzolakis et al. | 73/821 |
| 4,884,463 | 12/1989 | Kay | 73/865.8 |
| 5,152,055 | 10/1992 | L'Esperance, III et al. | 349/95 |
| 5,326,938 | 7/1994 | Tolson | 177/145 |

OTHER PUBLICATIONS

Erweka Brochure Entitled "Tablet Control Systems".
Vector Corporation Brochure Entitled "Tablet Testing Systems".

*Primary Examiner*—Robert Raevis
*Attorney, Agent, or Firm*—Buchanan Ingersoll, P.C.

[57] ABSTRACT

An apparatus and method for testing certain physical attributes of a medicinal tablet is provided in which the apparatus automatically positions the tablet in a proper orientation for a hardness test. In the test apparatus, the tablet to be tested is introduced to a linear guide track which moves the tablet from a thickness tester station to a weight tester station and finally to a hardness tester station. In the hardness tester station, the orientation of the tablet is visually inspected by means of a camera. A processing unit compares the orientation of the tablet with a predetermined orientation for a similarly-shaped tablet. The position of the tablet is then rotated so that the tablet is properly oriented. A ram and anvil are then brought into contact with the tablet and the ram and anvil are progressively forced together until the tablet is crushed. The maximum force needed to crush the tablet is measured and recorded.

9 Claims, 7 Drawing Sheets

METHOD AND APPARATUS FOR TESTING A MEDICINAL TABLET

BACKGROUND OF THE INVENTION

1. Field of the Invention

The present invention relates to an apparatus for testing a medicinal tablet, and, more particularly, to an apparatus suitable for conducting quality control tests of the thickness, weight, and hardness of medicinal tablets.

2. Background of the Invention

In order to maintain and document the quality of medicinal tablets, pharmaceutical companies are required to perform physical tests on select portions of production quantity runs of pharmaceutical tablets. These selected tablets may be chosen at random from the production line or may be chosen according to a more precise and controlled schedule. The tablets that are selected for testing are subjected to certain physical and chemical tests to insure that the tablets meet the criteria established by the pharmaceutical company in seeking FDA approval for the medicinal tablet.

Among the physical tests performed on the medicinal tablet are thickness, weight, and hardness measurements. The thickness, weight, and hardness of the medicinal tablet are important physical criteria which determine the dosage of the medicine provided in each medicinal tablet as well as the solubility of the medicinal tablet. The dosage of medicine in each tablet and solubility of the tablet must be consistent with the criteria established by the pharmaceutical company in seeking FDA approval for its medicinal compound.

In order to automate the physical testing of the tablet, certain apparatus have been previously developed and sold. Such apparatus are designed to receive a tablet and move the tablet among three separate testing stations, one station for each of the thickness, weight, and hardness measurements. The testing stations can be arranged on either a linear path along a top surface of the apparatus or along a circular or rotary path.

A problem frequently encountered with such automated apparatus is the alignment of the medicinal tablet for hardness testing. When seeking FDA approval, a pharmaceutical company tests the hardness of the tablet by crushing the tablet along a predetermined axis, usually the longest diagonal axis presented in the tablet. Accordingly, any automated testing apparatus must align the tablet in the hardness tester such that the hardness tester crushes the tablet along the same predetermined axis. If the tablet is not properly aligned, the tablet will be crushed along a different axis, thereby providing potentially inaccurate hardness measurements. Accordingly, there is a need for an apparatus which will automatically position an irregularly-shaped tablet in a hardness tester such that the force needed to crush the tablet along the predetermined axis is measured.

SUMMARY OF THE INVENTION

An apparatus is provided for testing a medicinal tablet in which a feeder conveys the tablet to the apparatus. A linear guide track is provided on the apparatus and is used to convey the tablet to a plurality of testing stations. This linear guide track includes a plurality of receptacle units which receive the tablet from the feeder and convey the tablet to each of the plurality of testing stations. A first receptacle in the linear guide track receives the tablet and conveys the tablet to a tablet thickness tester. A second receptacle on the linear guide track conveys the tablet from the thickness tester to the weight tester. Finally, a third receptacle on the linear guide track conveys the tablet from the weight tester to the hardness tester.

In order to align the tablet, the tablet hardness tester includes a rotatable platen upon which the tablet is initially positioned. A visual identifier, such as a camera, records the orientation of the tablet on the platen. The visually identified orientation of the tablet is compared with proper orientations for a similarly shaped tablet. The platen is then rotated until the tablet is oriented consistent with that predetermined orientation. An anvil is then positioned so that it supports one side of the oriented tablet. A ram, which provides the crushing force on the tablet, is then positioned from a side opposite the anvil so that both the anvil and the ram are in contact with the tablet. The ram is then forced against the tablet. The anvil supports the tablet until the tablet is crushed and the force needed to crush the tablet is measured and recorded.

DETAILED DESCRIPTION OF THE PREFERRED EMBODIMENTS

Figure 1:
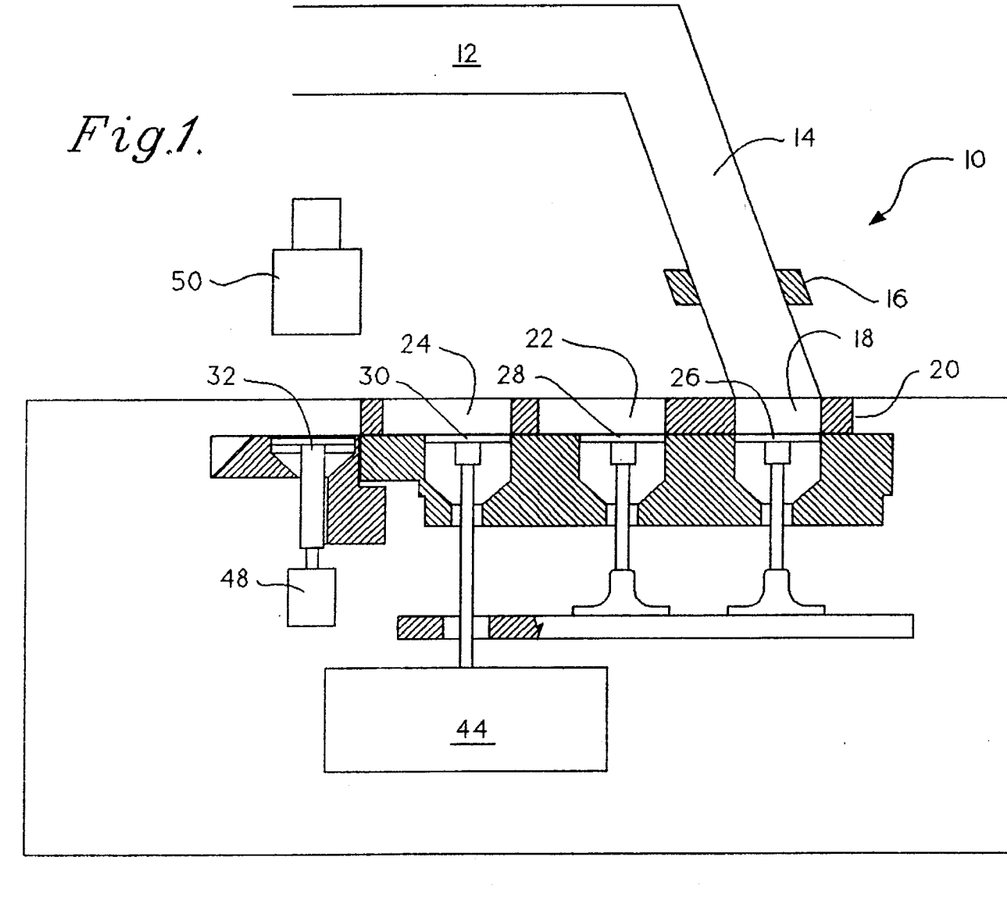
FIG. 1 is a front elevational view partially in cross-section of a presently preferred embodiment of the medicinal tablet testing apparatus of the present invention.

The presently preferred apparatus according to the present invention is illustrated in FIG. 1. Therein, apparatus 10 includes a feeder 12 having a chute 14 for introducing a tablet to the apparatus 10. A sensor 16 placed in chute 14 is used to indicate passage of a tablet from feeder 12 to the apparatus 10. The tablet is received by receptacle 18 provided in a linear guide track 20. As presently designed, linear guide track 20 also includes receptacles 22 and 24. Linear guide track 20 conveys the medicinal tablet from receiving station 26 to testing stations 28, 30, and 32. Preferably, guide track 20 does not have a top or bottom surface. Thus, receptacles 18, 22, and 24 are chambers formed solely of side walls, having no top or bottom surface. Alternatively, chute 14 can deliver the medicinal tablet directly to testing station 28, avoiding the need for a receiving station 26.

Linear guide track 20 is adapted to move linearly upon vertical indexer 34, which is adapted to move vertically relative to apparatus 10. The movements of linear guide track 20 and vertical indexer 34 in conveying a medicinal tablet 36 are shown schematically in FIGS. 2 through 8. The operation of linear guide track 20 and vertical indexer 34 in conveying tablet 36 to the various testing stations is discussed below.

Figure 2:
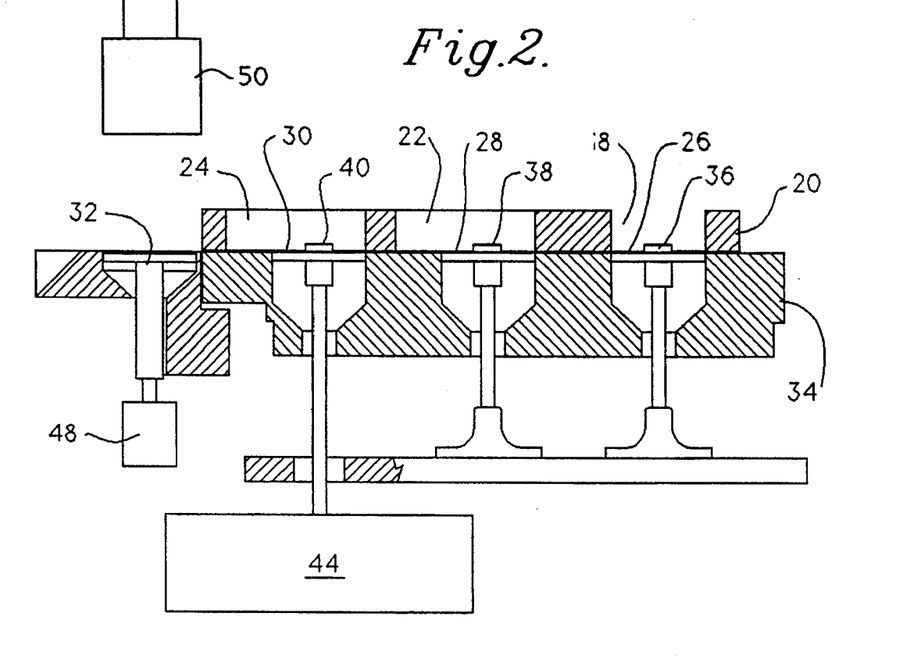
FIGS. 2–8 are sequential schematic cross-sectional views of a presently preferred tablet conveying mechanism used in the apparatus of FIG. 1 showing the steps in conveying the tablet between the testing stations.

In operation, as shown in FIG. 2, a first tablet 36 is introduced into receiving station 26 through receptacle 18 of linear guide track 20. Second tablet 38 has already been conveyed to thickness testing station 28 and third tablet 40 has already been conveyed to weight testing station 30. Sensor 16, shown in FIG. 1, signals the arrival of tablet 36 in receiving station 26, thereby beginning the sequence of operation of linear guide track 20 and vertical indexer 34.

Figure 3:
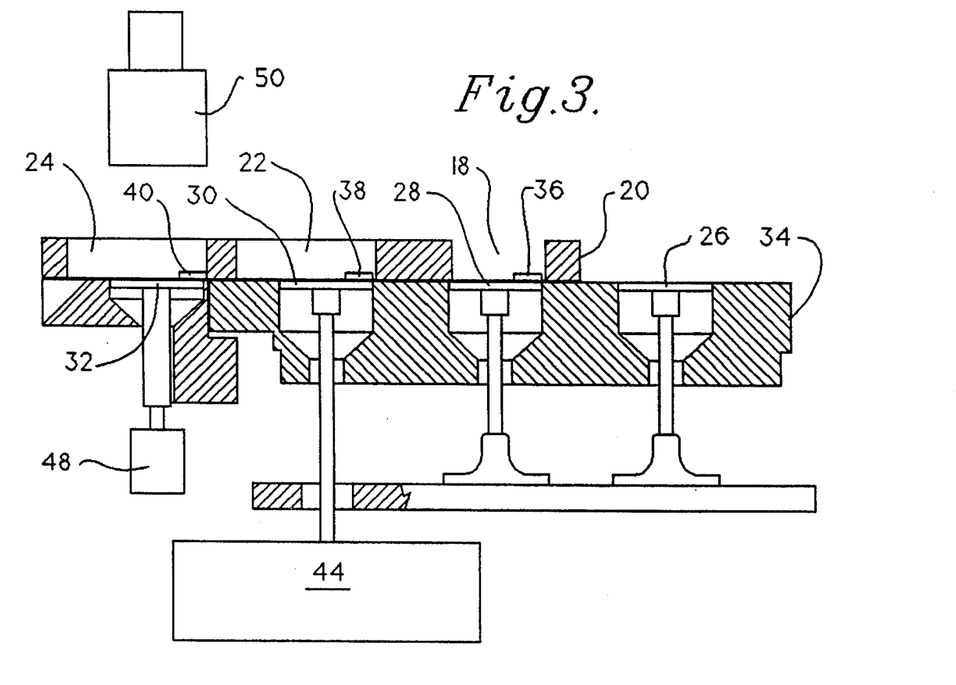

As shown in FIG. 3, as guide track 20 makes its first linear slide along vertical indexer 34, receptacle 18 transports the first tablet 36 from receiving station 26 to tablet thickness testing station 28. In a like manner, receptacle 22 transports second tablet 38 from tablet thickness testing station 28 to tablet weight testing station 30 and receptacle 24 transports third tablet 40 from tablet weight testing station 30 to tablet hardness testing station 32.

Figure 4:
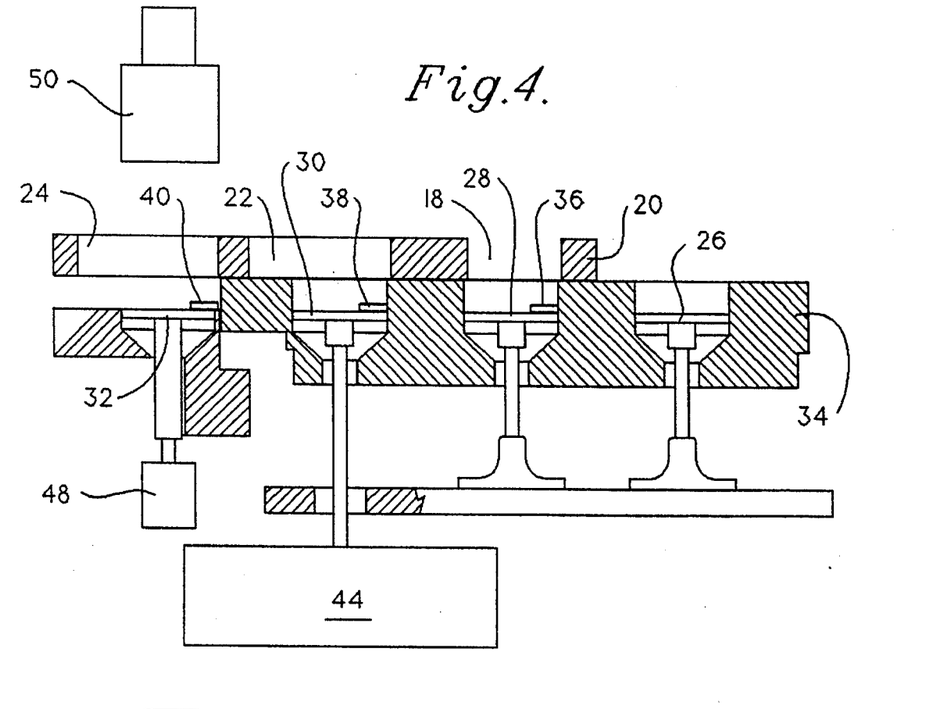
Figure 5:
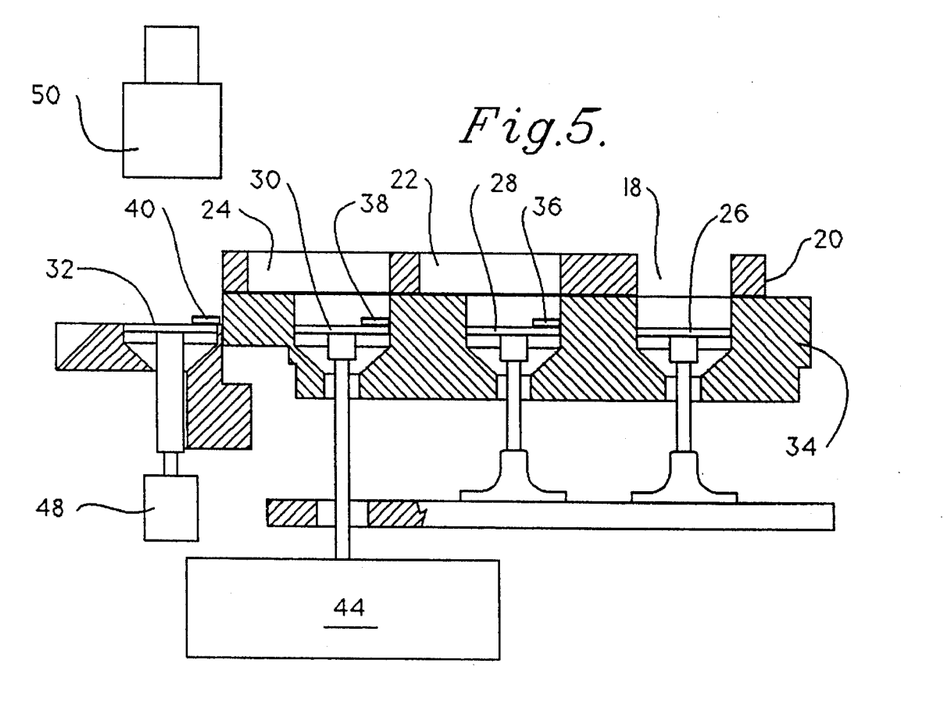
Figure 6:
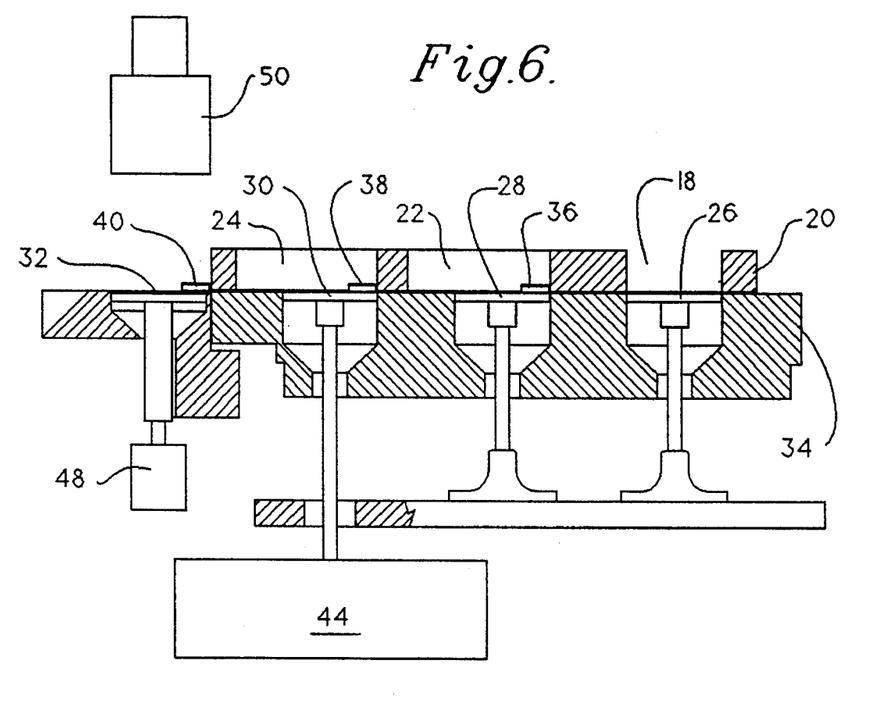
Figure 7:
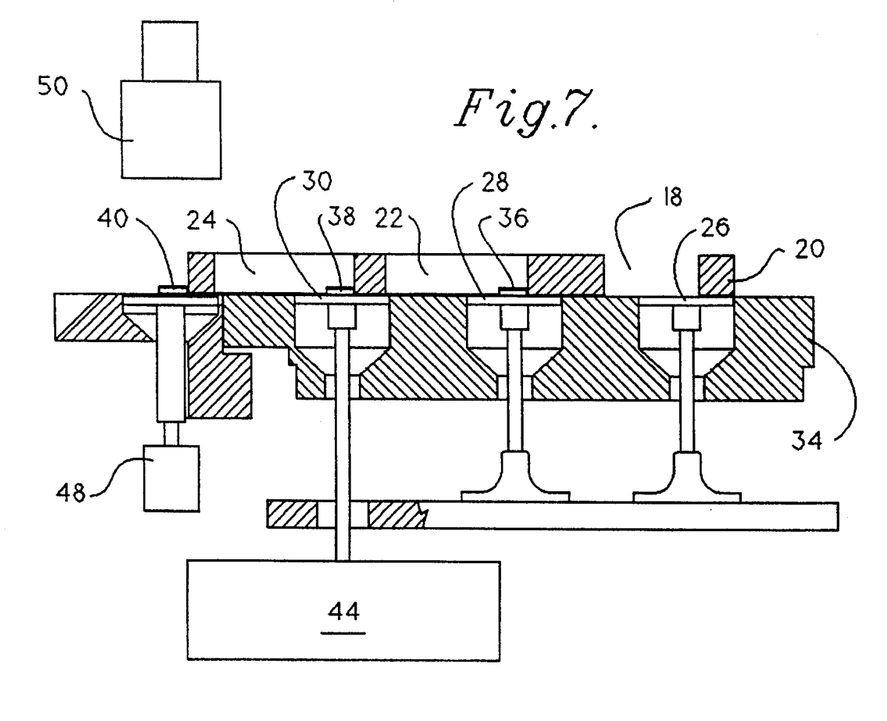

In order to properly position tablets 36, 38, and 40 in testing stations 28, 30, and 32, respectively, vertical indexer 34 moves vertically upward as shown in FIG. 4, carrying-linear guide track 20 with it. As shown in FIG. 5, linear guide track 20 then returns to its original position relative to vertical indexer 34. Then, as shown in FIG. 6, vertical indexer 34 moves downward and returns to its original position. As shown in FIG. 7, linear guide track 20 then moves forward approximately one half the width of a testing station. By this movement, linear guide track 20 centers tablets 36, 38, and 40 on testing stations 28, 30, and 32, respectively. Linear guide track 20 then returns to its original position shown in FIG. 8 where it can receive a new tablet for testing.

Figure 9:
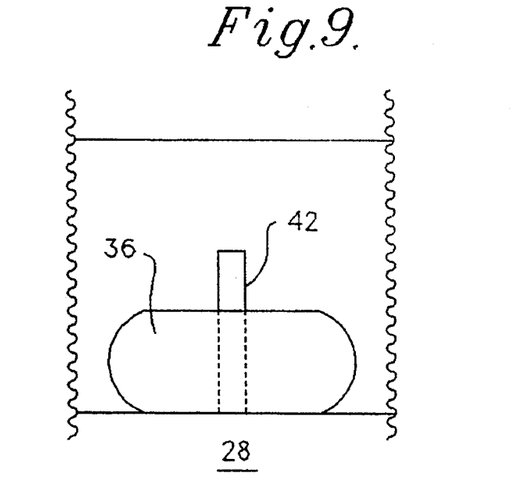
FIG. 9 is a cross-sectional view of a presently preferred embodiment of the thickness tester used in the apparatus of FIG. 1.

In the present apparatus 10, as shown in FIG. 9, the thickness of a tablet 36 is measured in test station 28 by means of a light transmitter, not shown. This measurement is taken once tablet 36 has been introduced into thickness testing station 28 as shown in FIG. 3. Tablet 36 blocks a portion of the light generated by the light transmitter. The thickness of tablet 36 is determined by measuring the reduction in the amount of light transmitted to light sensor 42. In order for thickness tester 28 to successfully operate, receptacle 18 must be designed without side walls or have side walls made of a clear transparent material which will not block light transmission therethrough.

Figure 8:
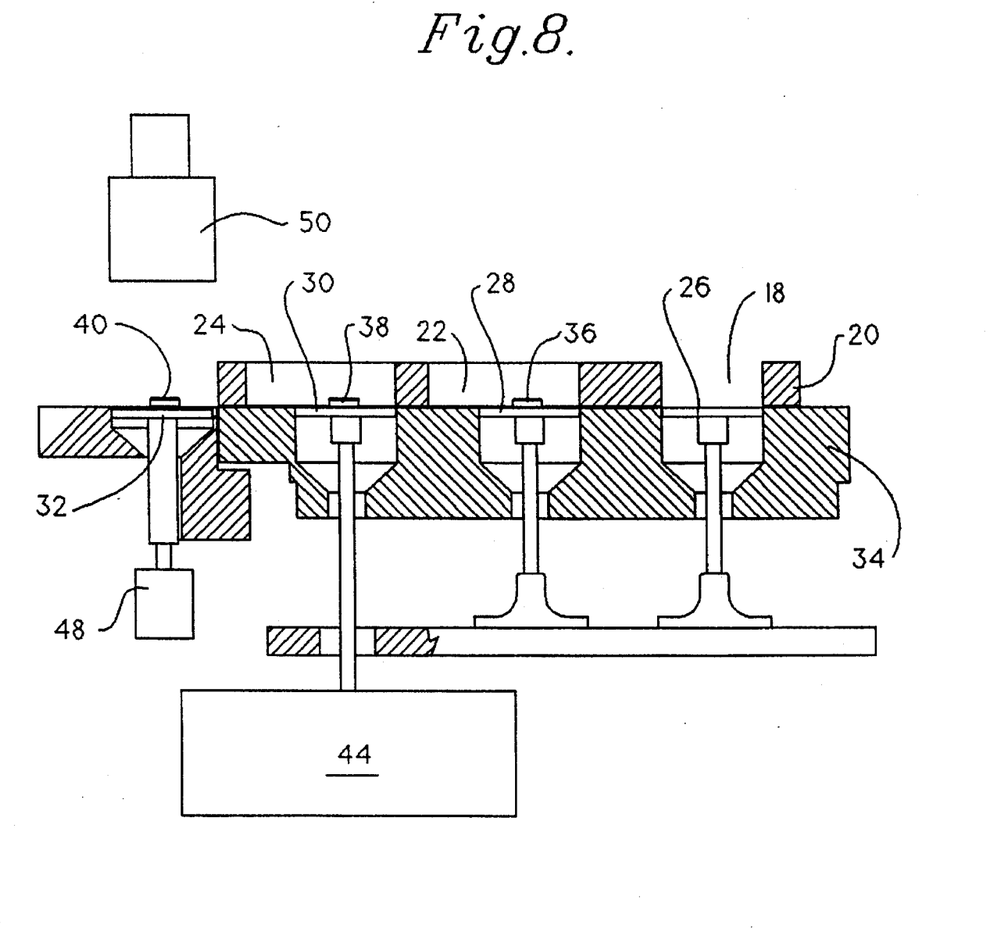

Preferably, the second testing station is weight testing station 30. Preferably, the weight measurement is not taken until tablet 38 is centered in weight testing station 30 as shown in FIG. 8. The weight measurement is taken of tablet 38 by means of a typical scale 44 such as manufactured by Mettler under the designation AM 50.

Figure 10:
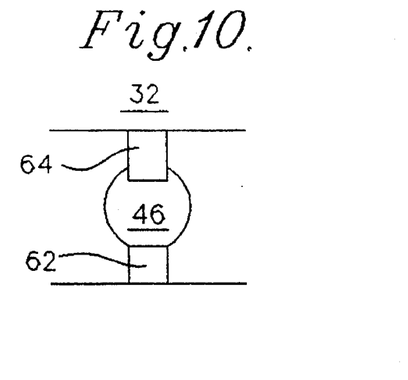
FIG. 10 is a top plan view of a presently preferred embodiment of the hardness tester used in the apparatus of FIG. 1.

After the weight of tablet 38 is measured, the hardness of tablet 40 can be measured in hardness testing station 32. As shown in FIG. 10, hardness testing station 32 includes a rotatable platen 46 driven by motor 48 upon which the centered tablet 40 is positioned. A camera 50, shown in FIG. 1, is positioned so that its field of vision is-centered on platen 46. In the arrangement shown in FIGS. 1 through 9, camera 50 is directed downward on station 32. Alternatively, the camera 50 can be directed parallel to the surface of hardness testing station 32 and a prism (not shown) can be used to direct the field of vision of camera 50 downward upon platen 46. Any type of video camera can be used for this purpose. Applicants have found that a RAGY CCD camera suitably performs the visual inspection task required for aligning the tablet 40.

Figures 12, 13, 14:
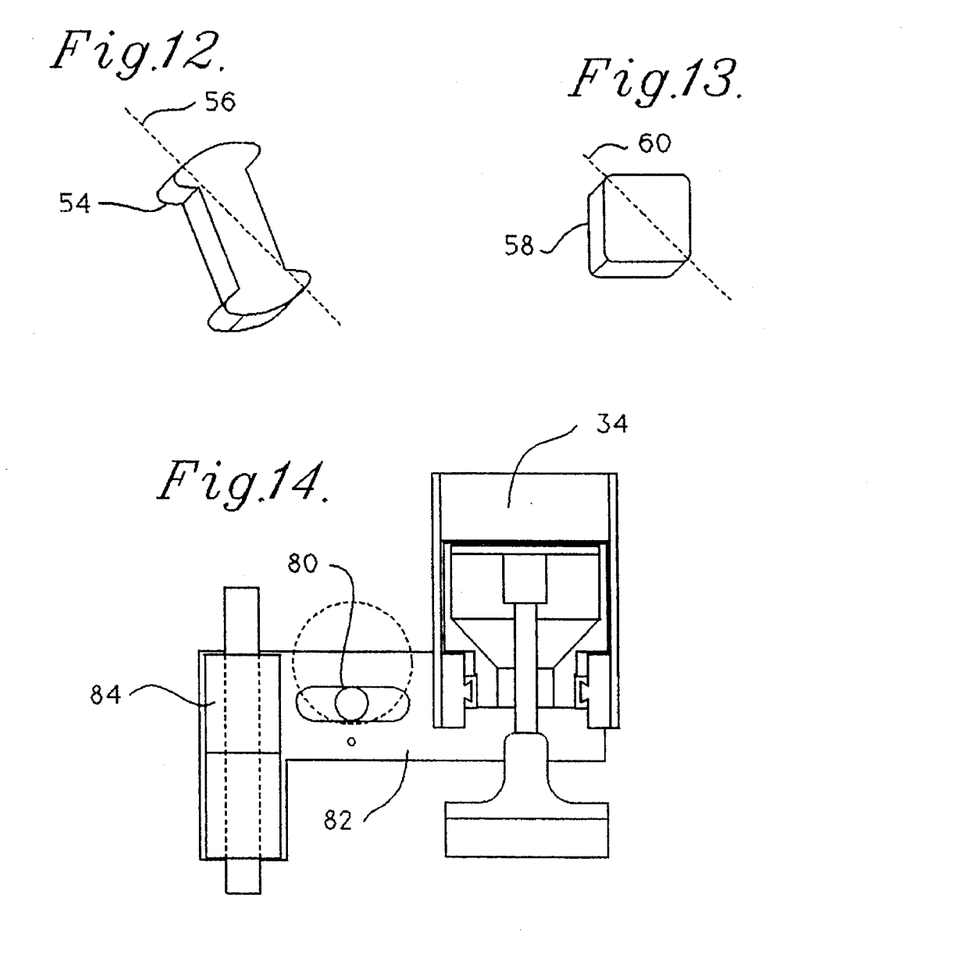
FIG. 12 is a representation of a first medicinal tablet showing the axis along which the tablet will be crushed.
FIG. 13 is a representation of a second medicinal tablet showing the axis along which the tablet will be crushed.
FIG. 14 is a schematic representation of the mechanism for driving the vertical indexer used in the apparatus of FIG. 1.

Camera 50 records the orientation of tablet 40 on the surface of rotatable platen 46. A motor 48 shown in FIG. 1 is used to rotate platen 46 so that tablet 40 is aligned in a proper orientation for hardness testing. Tablet 40 is properly oriented when the crushing force on the tablet is along a predetermined axis, in this case the longest diagonal axis of the tablet. FIGS. 12 and 13 illustrate this principle. In FIG. 12, irregularly shaped tablet 54 is shown having crushing axis 56. In FIG. 13, irregularly shaped tablet 58 is shown having its crushing axis 60. Although FIGS. 12 and 13 illustrate crushing the tablet along the longest diagonal axis present on the tablet, any axis of the tablet can be chosen as the predetermined axis.

Once platen 46 is rotated such that the tablet 40 is properly oriented, anvil 64, shown in FIG. 10, is positioned so that it contacts one side of the tablet 40 along the crushing axis. Ram 62 is then positioned to contact the opposing side of tablet 40. Once ram 62 and anvil 64 are positioned in abutting relationship to tablet 40, the force on ram 62 or, alternatively, anvil 64 and ram 62, is progressively increased until tablet 40 breaks apart. The force needed to crush tablet 40 is measured and recorded.

In order to properly orient tablet 40 on platen 46, the visual image of tablet 40 recorded by camera 50 is processed by a processing unit which compares the orientation of tablet 40 with predetermined proper orientations for similarly-shaped tablets. The processing unit is a software driven unit which is provided with data regarding the predetermined orientation of the various-shaped tablets 40. Once tablet 40 is properly oriented, visual camera 50 records the position of tablet 40 and the processor uses that position information to advance ram 62 and anvil 64 into contact with tablet 40.

Figure 11:
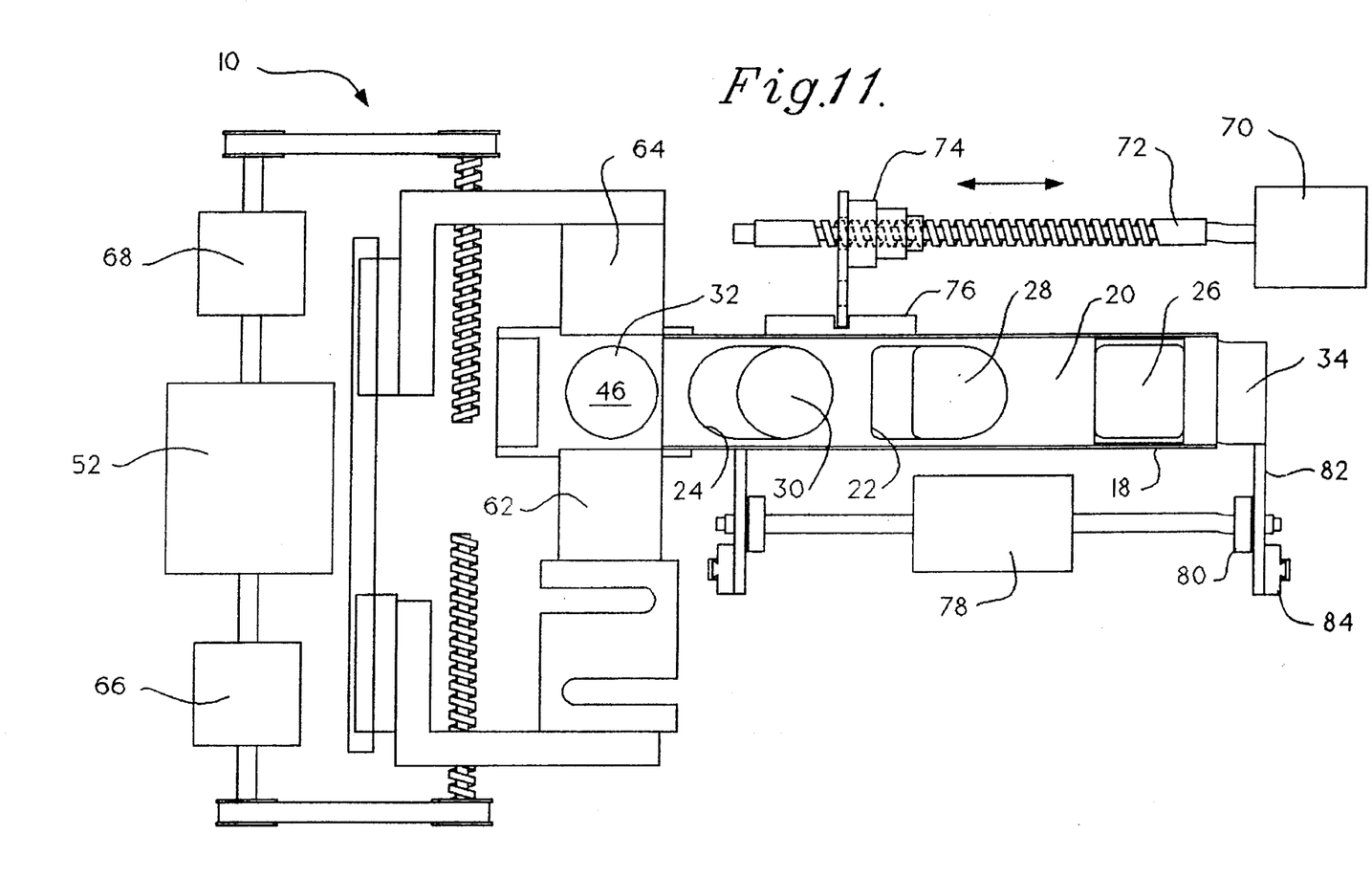
FIG. 11 is a top plan view, partially in section, of the apparatus of FIG. 1.

Preferably, as shown in FIGS. 1, 11 and 14, apparatus 10 utilizes stepper motors to control all the movements in the apparatus. Alternatively, such motors can be direct drive motors which do not use clutches. A first motor 48 rotates platen 46 and is described above. A second motor 52 is responsible for the hardness test function. In the hardness test, ram 62 and anvil 64 are used to crush a tablet while the force needed to crush the tablet is monitored. The maximum force represents the tablet's hardness. Two electromagnetic clutches 66 and 68 are used to allow independent movement of the ram 62 and anvil 64 respectively. Simultaneous movement of ram 62 and anvil 64 is possible by engaging both clutches.

The hardness test function motor 52 is wired so that clockwise direction of motor 52 results in ram 62 moving towards the center of hardness test chamber 32 and a counterclockwise direction results in ram 62 moving away from the center of test chamber 32. Anvil 64 is likewise moved towards and away from test chamber 32 by a clockwise and counterclockwise direction of motor 52, respectively. When both the ram and anvil clutch 66 and 68 are engaged, a clockwise motor direction results in ram 62 and anvil 64 moving towards each other.

A third motor 70 is used to control the indexing of the linear guide track 20. This motor 70 drives horizontal index screw 72 which is secured to horizontal index bolt 74. Rotation of motor 70 rotates screw 72 which causes bolt 74 to move linearly with respect to vertical indexer 34. Bolt 74 is connected to linear guide track 20 by means of horizontal index follower 76. By this connection, motor 70 controls the linear movement of linear guide track 20. Alternatively, belts or solenoids can be used to produce and control the horizontal movement of linear guide track 20.

A fourth motor used in apparatus 10 is motor 78 which controls the movement of vertical indexer 34. As shown in FIGS. 11 and 14, motor 78 acts on vertical cam 80 and vertical cam follower 82 to move vertical slide block 84. Vertical slide block 84 is connected to vertical indexer 34 and allows motor 78 to move vertical indexer 34 up and down. Alternatively, belts or solenoids can be used to produce and control the vertical movement of vertical indexer 34.

A fifth motor used in apparatus 10, not shown, is exclusively provided for the tablet feeder 12. Feeder 12 is directly driven and involves no clutch. Feeder 12 is used to drop single tablets from the feeder into the tablet tester apparatus 10.

The general operation of feeder 12 is to use a vibration as the feeder rotates alternately clockwise and counterclockwise, thereby increasing the total amount of rotation on each iteration until a tablet falls or a certain time period expires.

Use of receptacles 18, 22, and 24 has been found to be useful in confining the tablet to a particular test station. Round tablets have been found to be particularly inclined to roll. The use of receptacles 18, 22, and 24 confines the tablets being tested within the receptacles positioned over the testing station and also provide a more orderly transport of the tablets from one testing station to the next. In addition, the use of the receptacles and vertical indexer 34 prevents chips of broken tablet produced from hardness testing station 32 from interfering with the measurement taken at weight testing station 30.

In addition to aligning tablets based on their shape, apparatus 10 can also be adapted to align a tablet based on surface characteristics, such as bisects on the surface of a round tablet. Camera 50 having a self-focussing function may be needed to reveal such surface characteristics. Using such surface characteristics, the processing unit directs the rotation of platen 46 to properly align the tablet.

In the foregoing specification certain preferred practices and embodiments of this invention have been set out, however, it will be understood that the invention may be otherwise embodied within the scope of the following claims.

We claim:

1. An apparatus for testing a medicinal tablet said apparatus having a plurality of testing stations, said apparatus comprising:
   a. a feeder for receiving said tablet and conveying said tablet to said plurality of testing stations of said apparatus;
   b. a linear guide track along which said tablet is conveyed to said plurality of testing stations, said linear guide track comprising a plurality of receptacle units for receiving said tablet from said feeder and conveying said tablet to each of said plurality of testing stations;
   c. a tablet thickness tester provided at one of said plurality of testing stations;
   d. a tablet weight tester provided at one of said plurality of testing stations; and
   e. a tablet hardness tester provided at one of said plurality of testing stations, said tablet hardness tester comprising:
      i. a rotatable platen upon which said tablet is positioned;
      ii. a visual identifier for recording the orientation of said tablet on said platen;
      iii. means for rotating said platen to adjust the orientation of said tablet on said platen to a predetermined orientation;
      iv. processing means for comparing the recorded orientation of said tablet on said platen with said predetermined orientation to control rotation of said platen;
      v. an anvil which supports one side of said oriented tablet and a ram which provides a crushing force from a side opposite said one side of said tablet;
      vi. means for positioning said anvil and ram to crush said tablet; and
      vii. means for recording the force needed to crush said tablet.

2. The apparatus of claim 1 wherein said linear guide track includes a horizontal indexer and a vertical indexer, wherein said receptacle units are provided in said horizontal indexer, and said vertical indexer is adapted to raise and lower said horizontal indexer with respect to said plurality of testing stations, said horizontal indexer adapted to move horizontally upon said vertical indexer.

3. The apparatus of claim 2 wherein said horizontal indexer comprises:
   a. a first receptacle unit for receiving said tablet from said feeder and conveying said tablet to a first of said plurality of testing stations;
   b. a second receptacle unit for conveying said tablet from said first of said plurality of testing stations to a second of said plurality of testing stations; and
   c. a third receptacle unit for conveying said tablet from said second of said plurality of testing stations to a third of said plurality of testing stations.

4. The apparatus of claim 1 wherein said visual identifier is a video camera.

5. An apparatus for testing the hardness of a medicinal tablet comprising:
   a. a rotatable platen upon which said tablet is positioned;
   b. a visual identifier for recording the orientation of said tablet on said platen;
   c. means for rotating said platen to adjust the orientation of said tablet on said platen to a predetermined orientation;
   d. processing means for comparing the recorded orientation of said tablet on said platen with said predetermined orientation to control rotation of said platen;
   e. an anvil which supports one side of said oriented tablet and a ram which provides a crushing force from a side opposite said one side of said tablet;
   f. means for positioning said anvil and ram to crush said tablet; and
   g. means for recording the force needed to crush said tablet.

6. The apparatus of claim 5 wherein said visual identifier is a video camera.

7. A method for testing a medicinal tablet comprising the steps of:
   a. feeding said tablet to a test apparatus;
   b. conveying said tablet along a linear guide track to a plurality of testing stations;
   c. measuring the thickness of said tablet at one of said plurality of testing stations;
   d. measuring the weight of said tablet at one of said plurality of testing stations; and
   e. measuring the hardness of said tablet at one of said plurality of testing stations, said tablet hardness being measured by the steps of:
      i. positioning said tablet upon a rotatable platen;

ii. visually recording the orientation of said tablet on said platen;
iii. comparing said recorded orientation to a predetermined orientation of said tablet;
iv. rotating said platen to adjust the orientation of said tablet on said platen to said predetermined orientation;
v. positioning an anvil adjacent one side of said oriented tablet to support said tablet;
vi. positioning a ram against a side opposite said one side of said tablet;
vii. moving said ram against said tablet to crush said tablet; and
viii. recording the force needed to crush said tablet.

8. The method of claim 7 wherein said linear guide track:
a. receives said tablet from said feeder and conveys said tablet to a first of said plurality of testing stations;
b. conveys said tablet from said first of said plurality of testing stations to a second of said plurality of testing stations; and
c. conveys said tablet from said second of said plurality of testing stations to a third of said plurality of testing stations.

9. A method for measuring the hardness of a medicinal tablet comprising the steps of:
a. positioning said tablet upon a rotatable platen;
b. visually recording the orientation of said tablet on said platen;
c. comparing said recorded orientation of said tablet to a predetermined orientation of said tablet;
d. rotating said platen to adjust the orientation of said tablet on said platen to said predetermined orientation;
e. positioning an anvil adjacent said oriented tablet to support one side of said tablet;
f. positioning a ram against a side opposite said one side of said tablet;
g. moving said ram against said tablet to crush said tablet; and
h. recording the force needed to crush said tablet.

* * * * *